United States Patent [19]
Alden et al.

[11] Patent Number: 5,984,942
[45] Date of Patent: Nov. 16, 1999

[54] METHODS AND SYSTEMS FOR REDUCING TISSUE ADHESION

[75] Inventors: Donald L. Alden, Sunnyvale; George M. Savage; Arnold J. Kresch, both of Portola Valley, all of Calif.

[73] Assignee: FemRx, Inc., Sunnyvale, Calif.

[21] Appl. No.: 08/832,014

[22] Filed: Apr. 2, 1997

[51] Int. Cl.⁶ ................................................. A61B 17/00
[52] U.S. Cl. ..................... 606/190; 606/192; 600/207
[58] Field of Search ............... 604/96–101; 606/191, 606/194, 195, 192, 198, 190; 600/207

[56] References Cited

U.S. PATENT DOCUMENTS

| | | | |
|---|---|---|---|
| 4,484,579 | 11/1984 | Meno et al. | 606/194 |
| 4,800,901 | 1/1989 | Rosenberg . | |
| 5,120,322 | 6/1992 | Davis et al. . | |
| 5,192,296 | 3/1993 | Bhate et al. . | |
| 5,290,247 | 3/1994 | Crittenden . | |
| 5,366,472 | 11/1994 | Hillstead . | |
| 5,387,224 | 2/1995 | Semm . | |
| 5,425,760 | 6/1995 | Rosenberg . | |
| 5,452,732 | 9/1995 | Bircoll | 606/192 |
| 5,458,572 | 10/1995 | Campbell et al. . | |
| 5,540,711 | 7/1996 | Kieturakis et al. | 606/190 |
| 5,549,625 | 8/1996 | Bircoll | 606/192 |
| 5,607,443 | 3/1997 | Kieturakis et al. | 606/192 |
| 5,720,762 | 2/1998 | Bass | 606/192 |
| 5,779,728 | 7/1998 | Lunsford et al. | 606/190 |

FOREIGN PATENT DOCUMENTS

| | | |
|---|---|---|
| 0 461 474 | 12/1991 | European Pat. Off. . |
| 2 673 110 | 8/1992 | France . |
| 2 021 776 | 5/1992 | Russian Federation . |

*Primary Examiner*—Michael Buiz
*Assistant Examiner*—William Lewis
*Attorney, Agent, or Firm*—Verne E. Kreger, Jr.

[57] ABSTRACT

The invention provides systems and methods for interfering with the adhesion formation process. In some embodiments, the present invention makes use of intermittent blunt dissection of fibrin bridging adjacent tissues prior to the formation of adhesions. Dissection is generally provided by pulsing a balloon implanted between the tissues. Optionally, the balloon will comprise an elastic structure to disrupt the formation of fibrin between the balloon and the surrounding tissues. Alternatively, the balloon may be at least partially covered by a bio-active anti-adhesion material. In some embodiments, the anti-adhesion material forms an envelope which is left between the tissues when the balloon is removed.

25 Claims, 5 Drawing Sheets

FIG. 1A
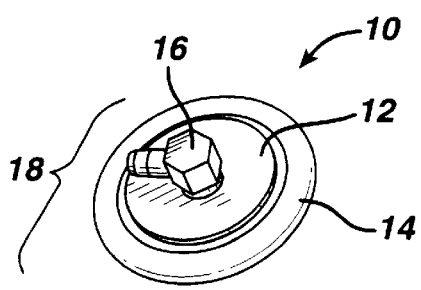
FIG. 1B
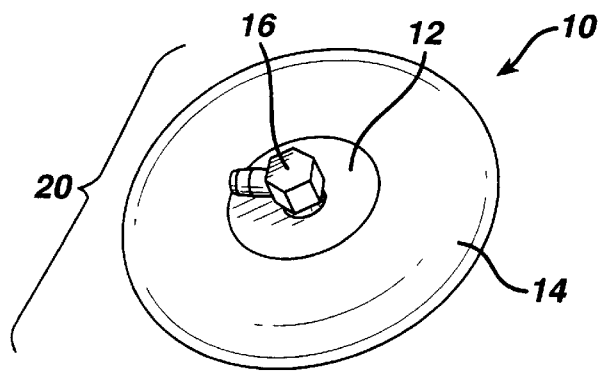
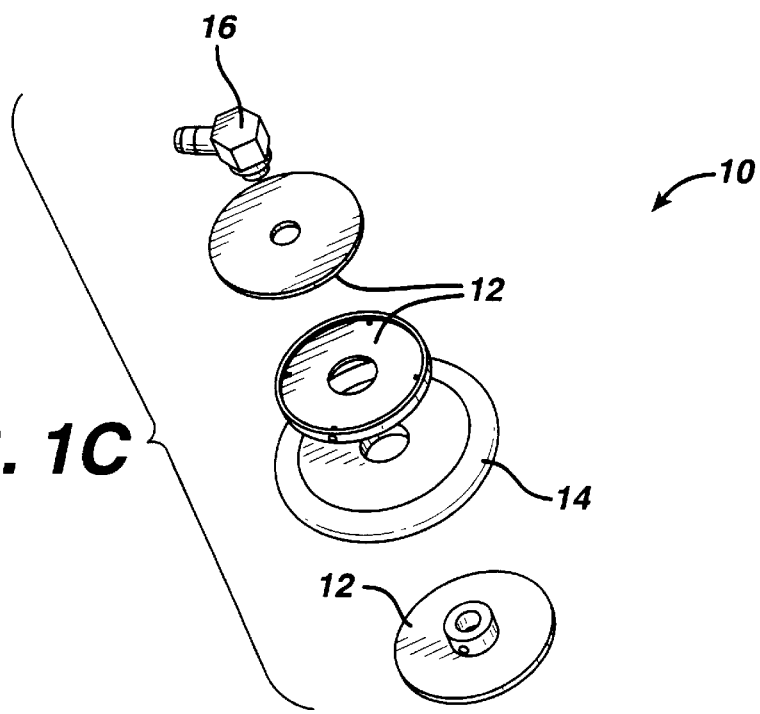
FIG. 1C

METHODS AND SYSTEMS FOR REDUCING TISSUE ADHESION

BACKGROUND OF THE INVENTION

1. Field of the Invention

This invention relates generally to surgery and post-surgical care, and in particular, provides methods and devices which avoid the formation of adhesions between internal organs and tissues, particularly after surgery.

Post-operative adhesion formation is a major clinical problem after many abdominal, pelvic, thoracic, and other surgical procedures. As the body heals from the trauma of surgery, blood components surround the injured tissue to close the wound. Specifically, free white blood cells and platelets arrange themselves into a regular mesh structure called fibrin. Fibrin promotes healing by knitting traumatized tissues together to close wounds. Tissue then grows on this fibrin substrate.

Unfortunately, fibrin often extends between adjacent tissues at the surgical site. Tough fibrous bands of scar tissue, called "adhesions," may form between organs and tissue layers which normally slide with respect to each other. These bands can lock such tissues in a fixed relative position, causing considerable pain and other morbidity as they pull internally.

Once adhesions are formed, the affected tissues are normally separated through further surgery using sharp dissection. Unfortunately, this follow-on surgery can cause further bleeding, which promotes formation of still further adhesions.

It has recently been proposed to introduce an air cushion-like structure to maintain mechanical separation for prevention of post-operative adhesion formation. While maintaining such mechanical separation can prevent adhesion formation between the tissues which are held apart, such a procedure involves continuously displacing tissues from a time period between a few hours and several days. Such prolonged tissue displacement may itself cause considerable pain, and may be detrimental to the healing process. Additionally, only those tissues which are held apart by the air cushion device will be affected, and fibrin may form between the air cushion device and the surrounding tissues, potentially leading to the formation of adhesions which lock the air cushion in place. Such adhesions would complicate removal of the air cushion, and would increase the probability that bleeding and additional adhesion formation will occur after the device is removed.

An alternative mechanism to prevent the formation of adhesions is to separate the tissues with a thin film of bio-active anti-adhesion material. These anti-adhesion materials may be bio-absorbable, avoiding any post-operative follow-up surgery, or they may be permanent. Anti-adhesion materials have been approved by the Food and Drug Administration and are commercially available under the trade names Interceed® and Seprafilm®, which have been shown to be effective. Nonetheless, these materials may produce allergic reactions in some patients. White cells and platelets can also migrate to the edges of these films, resulting in adhesion formation despite the presence of the anti-adhesion material. Additionally, deployment of these thin films may be problematic in certain procedures, particularly when using minimally invasive surgical techniques, and subsequent movement of these films from the target area may leave tissues unprotected.

In light of the above, it would be desirable to provide improved methods and systems for the prevention of adhesion formation. It would be preferable if such systems and methods were adaptable for patients who are intolerant to known anti-adhesion materials. It would also be preferable if such improved techniques minimized discomfort for recovering patients, thereby promoting the post-operative healing process.

2. Description of the Background Art

U.S. Pat. No. 5,387,244 describes an adhesion prophylaxis which maintains mechanical separation using an air cushion-like device. Anti-adhesion materials are commercially available from Ethicon of Somerville, N.J., under the trademark Interceed®, and from Genzyme of Cambridge, Mass. under the trademark Seprafilm®.

U.S. Pat. No. 5,120,322 describes a method and apparatus for treatment of fibrotic lesions using lathyrgenic agents. Russian Patent No. 2021776 describes a procedure for preventing post-operation hematoma and muscle/bone adhesions using a silicon tube with an antiseptic filled balloon.

French Patent No. 2673110 describes a balloon-tipped catheter designed to be inflated to hold a catheter in position after insertion. U.S. Pat. Nos. 5,425,760 and 4,800,901 describe balloon-type tissue expansion devices. European Patent No. 461474 describes a catheter with a balloon at its distal end having a spring elastic sleeve which is automatically retractable on balloon deflation.

U.S. Pat. No. 5,192,296 describes a dilation catheter, while U.S. Pat. No. 5,366,472 describes a dilation balloon within an elastic sleeve. U.S. Pat. Nos. 5,290,247 and 5,458,572 are generally relevant.

SUMMARY OF THE INVENTION

The present invention provides systems and methods for interfering with the adhesion formation process. In some embodiments, the present invention bluntly dissects fibrin bridging adjacent tissues prior to the formation of adhesions. Advantageously, by only intermittently separating these body structures, the tissues can heal largely at their nominal positions. Intermittent blunt dissection is typically provided by occasionally pulsing a balloon implanted between the tissues. The balloon may be at least partially covered by a bio-active anti-adhesion material. In some embodiments, the anti-adhesion material forms an envelope which is left between the tissues when the balloon is removed. Advantageously, the methods and systems of the present invention are particularly well suited for prevention of adhesion formation after invasive and minimally invasive surgical procedures.

In a first aspect, the present invention provides a method for interfering with formation of adhesions between two tissues. The tissues have nominal positions which are adjacent to each other within a patient body. The method comprises inflating a balloon to separate the tissues, and deflating the balloon to allow the tissues to return toward their nominal positions. These inflating and deflating steps are intermittently repeated during an adhesion prophylactic period.

Advantageously, the balloon need only be inflated momentarily to disrupt fibrin which bridges the tissues. Preferably, the balloon is inflated at an interval which is less than the time required for formation of adhesions between these tissues. Between these intermittent or "pulsed" inflations, displacement of the tissues and discomfort to the patient are minimized. The balloon will typically be removed after re-epithelialization of the traumatized tissue.

In another aspect, the present invention provides a method for controlling scar tissue formation. The method comprises inserting a balloon system into a patient body. A bio-active anti-adhesion material is disposed between at least a portion of the balloon system and surrounding tissues. The balloon is inflated within the patient body, deflated, and removed from the patient body. Optionally, the anti-adhesion material is bio-absorbable, and forms an envelope which initially covers the balloon, but which remains within the patient body when the balloon is removed. The balloon may be pulsed intermittently, as described above, or may alternatively be continuously inflated to maintain mechanical separation of the tissues.

In yet another aspect, the present invention provides a system for controlling the formation of adhesions between nominally adjacent tissues. The system comprises an implantable balloon and a pressurization system. The pressurization system is in fluid communication with the balloon for repeatedly inflating and deflating the balloon, either automatically or manually, so that the balloon intermittently separates the nominally adjacent tissues. Preferably, adhesion formation between the balloon and the surrounding tissues is prevented through the use of elastomeric balloon materials, or by covering at least a portion of the balloon with a bio-active anti-adhesion material. The use of elastomeric balloon materials is particularly preferred, as fibrin and adhesions may simply flex over an inflated inelastic structure. An elastic balloon will help break the fibrin and disrupt the forming adhesions.

In yet another aspect, the present invention provides a system for controlling the formation of adhesions between nominally adjacent tissues within a patient body. The system comprises a balloon which is implantable within the patient body. The balloon is inflatable to separate the nominally adjacent tissues, and a pressurization system is in fluid communication with the balloon for such inflation. An anti-adhesive material covers at least a portion of the balloon.

The present invention also provides a balloon for separating nominally adjacent tissues. The balloon comprises at least one elongate, serpentine tube, and the balloon defines a substantially flat panel when inflated.

BRIEF DESCRIPTION OF THE DRAWINGS

FIGS. 1A, 1B, and 1C are perspective views of a toroidal balloon structure for use in preventing the formation of adhesions, and are shown in a deflated configuration, an inflated configuration, and in an exploded view, respectively.

DETAILED DESCRIPTION OF THE SPECIFIC EMBODIMENTS

Figure 2A:
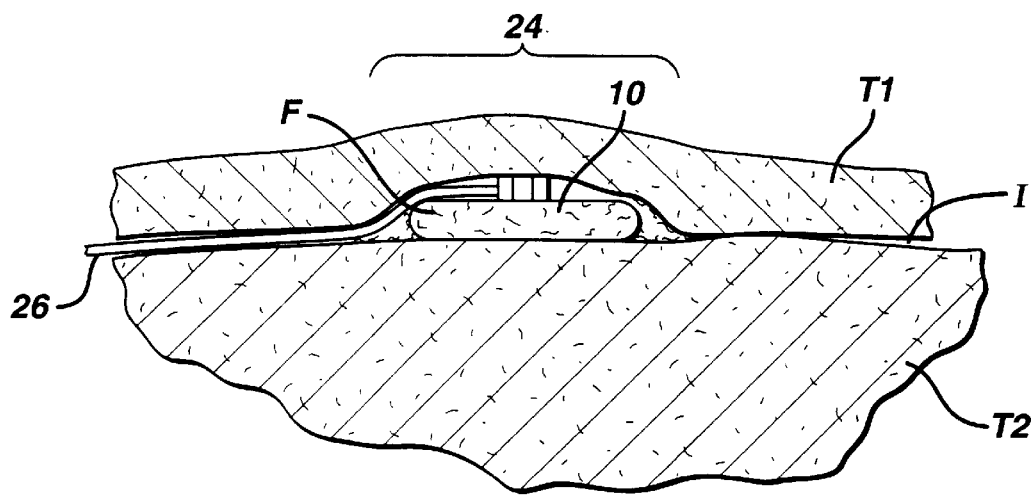
FIGS. 2A and 2B are partial cross-sections showing a method for using the balloon of FIGS. 1 by intermittently pulsing the balloon to bluntly dissect adjacent tissues so as to disrupt the fibrin prior to formation of adhesion tissues.

The present invention is capable of avoiding and minimizing the formation of adhesions after trauma to a wide variety of tissues, including those of the abdomen, pelvis, thorax, and the like. The methods and systems of the present invention will find their most immediate application as a post-operative adhesion prophylaxis following invasive or minimally invasive surgeries on peritoneal tissues.

Referring now to FIGS. 1A–C, a toroidal balloon 10 includes a non-distensible inner body 12 which supports elastomeric balloon 14. Balloon 14 extends circumferentially beyond inner body 12. The inner body limits axial expansion of the balloon membrane, holding balloon 14 to a substantially toroidal shape. A port 16 allows inflation of the balloon from a substantially flat, pancake-like uninflated configuration 18. In inflated configuration 20, the balloon increases in axial thickness and overall diameter.

The embodiment of the present balloon illustrated in FIGS. 1A–C is based on readily available components, and may be modified to ease delivery, removal, and to minimize trauma to the patient. For example, port 16 may be faired into inner body 12, rather than protruding axially. Additionally, although the inner body 12 shown here comprises substantially rigid materials, it may be advantageous to integrate the supply tube and inner body into a small, flexible package. For example, forming inner body 12 with a preset curl might facilitate rolling the deflated device into a smaller cross-section for removal through a small incision. Alternatively, an air cushion-like structure (such as that described in U.S. Pat. No. 5,387,224, the entire disclosure of which is incorporated herein by reference) might be used. Such an air cushion-like structure may be particularly well suited for replacing the rigid elements of inner body 12, allowing removal (and possibly insertion) of the balloon of the present invention with less trauma to the patient.

Methods for using the balloon of FIGS. 1 will be described with reference to FIGS. 2A and 2B. Balloon 10 has been implanted at an interface I between first and second tissues T1, T2. As described above, interface I will often allow relative motion when these tissues are healthy. To prevent the formation of adhesions connecting these tissues after first tissue T1, second tissue T2, or some adjacent tissue has been subjected to trauma, balloon 10 is inserted surgically, often during the surgical procedure which imposes the trauma on the tissues. An elongate body 26 allows remote actuation of the balloon, typically through a port in the skin. Inflation and deflation can be accomplished manually via a syringe in a manner similar to that used with a Foley bladder catheter balloon. In some embodiments, the proximal end of tubular body 26 may exit the tissue interface or body cavity via a subcutaneous tunnel, in a manner similar to that used for Chronic Ambulatory Pertoneal Dialysis (CAPD). Alternatively, the proximal end may be left in a subcutaneous space for retrieval under local anesthesia when it is time to pulse the balloon or withdraw the anti-adhesion system.

When balloon 10 is deflated, as illustrated in FIG. 2A, mechanical separation is provided between tissues T1 and T2 over a relatively, small first region 24. Advantageously, the displacement of the tissues by deflated balloon 10 is relatively minor. Although balloon 10 prevents the formations of adhesions directly between tissues T1 and T2 within first region 24, fibrin may begin to form between balloon 10 and each of the adjacent tissues, as well as between the tissues in interface I outside of first region 24.

In some embodiments, a coating of bio-active anti-adhesion material may coat at least a portion of balloon 10 to prevent the formation of adhesions between the balloon system and the surrounding tissues. Unfortunately, some patients may suffer from allergic reactions or other adverse side effects from these materials. In such patients, the formation of fibrin F over the outer surface of balloon 10 can be substantially disrupted by forming the balloon of an elastomeric material. When balloon 10 inflates, fibrin coating and/or attached to the elastic material will be stressed. As the balloon material expands, at least a portion of the fibrin is detached. In some embodiments, elastomeric material may coat substantially all of the balloon and/or balloon system, so as to expand during inflation of the balloon and disrupt fibrin attachment without provoking an allergic reaction.

Figure 2B:
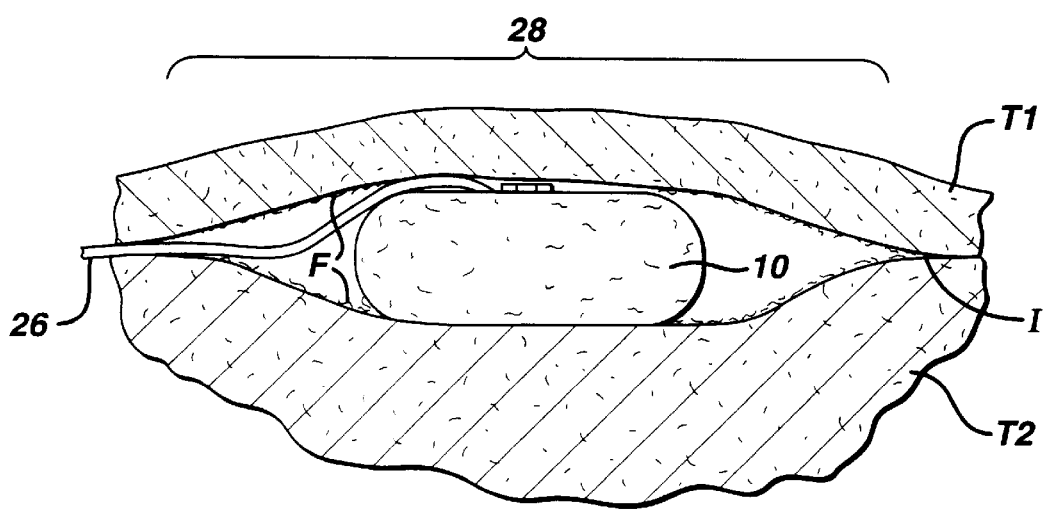

As illustrated in FIG. 2B, when balloon 10 is inflated through tubular body 26, fibrin F is disrupted over a second region 28 which is much larger than the small region which was mechanically separated and displaced by the uninflated balloon. While balloon 10 increases in both thickness and diameter, the expanded region of adhesion prophylaxis extends substantially radially beyond even the expanded balloon size. Moreover, while tissues T1 and T2 and momentarily displaced to a significant degree during inflation, after fibrin F has been disrupted, the balloon can then be deflated so that tissue displacement and patient discomfort are minimized.

Once the balloon is deflated, fibrin will again begin to bridge interface I between tissues T1 and T2. While this process will be begin fairly quickly, the total time between the initiation of fibrin formation and the completion of significant adhesion tissue formation can be quite substantial. For this reason, balloon 10 need only be pulsed intermittently, typically every 30.0 to 480.0 minutes. Generally, the balloon will be inflated for less time than it is deflated, preferably being inflated for a time of between 1.0 and 10.0 minutes. The balloon system will generally be in place for a time period of between 2.0 and 3.0 weeks. Inflation may proceed relatively slowly and be limited to times the patient is awake, and will often be controlled using an outside automatic controller.

Figure 3:
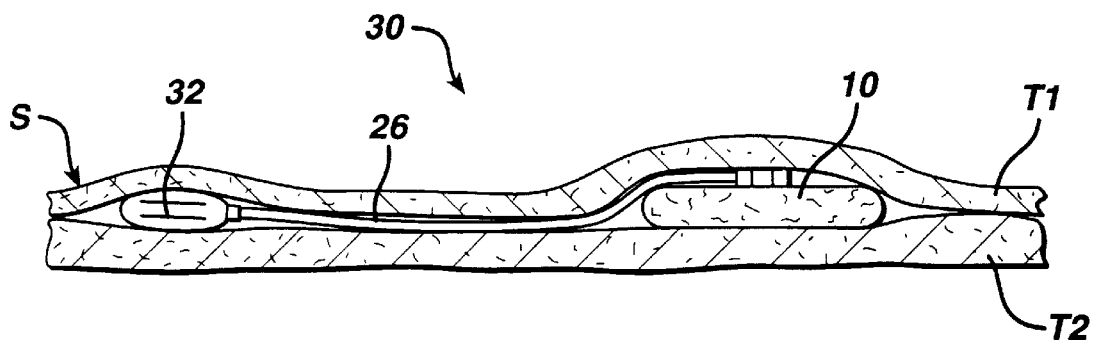
FIG. 3 is a partial cross-section showing a balloon system including the balloon of FIGS. 1, and also including a subcutaneous pump for actuation through the skin.

Referring now to FIG. 3, a subcutaneous balloon system 30 includes balloon 10 and a subcutaneous inflation pump 32. Pump 32 comprises a bulb which is implantable under the skin, and which is manipulatable through the skin to inflate and deflate balloon 10. Pump 32 may optionally have a reservoir associated therewith, and may be similar in structure and use to subcutaneous pumps used for erectile disfunction.

Figure 4A:
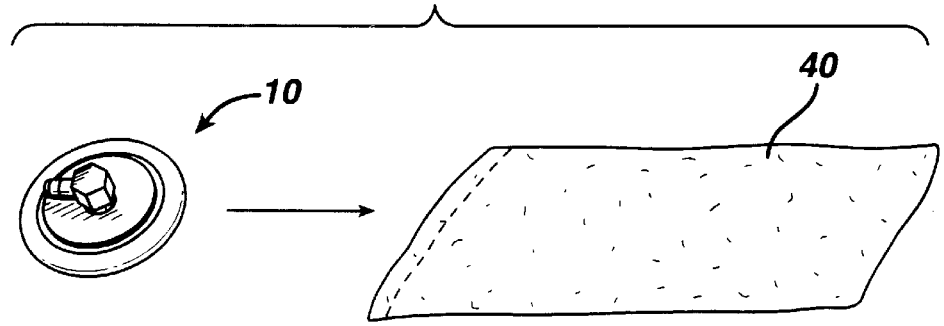
FIGS. 4A and 4B schematically illustrate a method for interfering with the formation of adhesions by removably covering the balloon of FIGS. 1 in an envelope of anti-adhesion material.
Figure 4B:
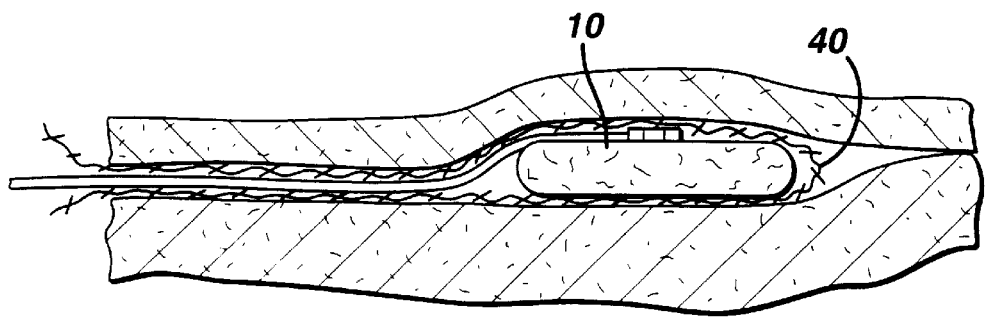

Referring now to FIG. 4A, an alternative embodiment of a anti-adhesion system includes a balloon 10 removably inserted within an envelope 40 formed of a bio-active anti-adhesion material. Such materials may be either bio-absorbable or permanently residing. By covering at least a portion of balloon 10 with such a anti-adhesion material, the present invention provides the advantages of mechanical separation from a continuously or intermittently inflated balloon with the efficacy of these bio-active materials, and also maintains the position and orientations of the envelope while healing begins. As generally described above, periodic or continuous mechanical separation of tissues T1 and T2 is generally maintained until re-epithelialization of the traumatized surfaces is complete. Where envelope 40 comprises a bio-absorbable material, balloon 10 and its associated system components may be removed easily, leaving the anti-adhesion material to provide residual efficacy and minimize trauma of the removal process. In some embodiments, the anti-adhesion material may already be absorbed by the patient before the balloon is removed.

In some embodiments, permanent or bio-absorbable anti-adhesion coatings may be simply bonded to the balloon system itself. Permanent anti-adhesion coatings and bio-absorbable anti-adhesion removable envelopes may also be combined to facilitate removal of any portion of the mechanical separation system extending beyond the envelope, as well as any portions which are exposed when some or all of the envelope is absorbed.

Figure 5A:
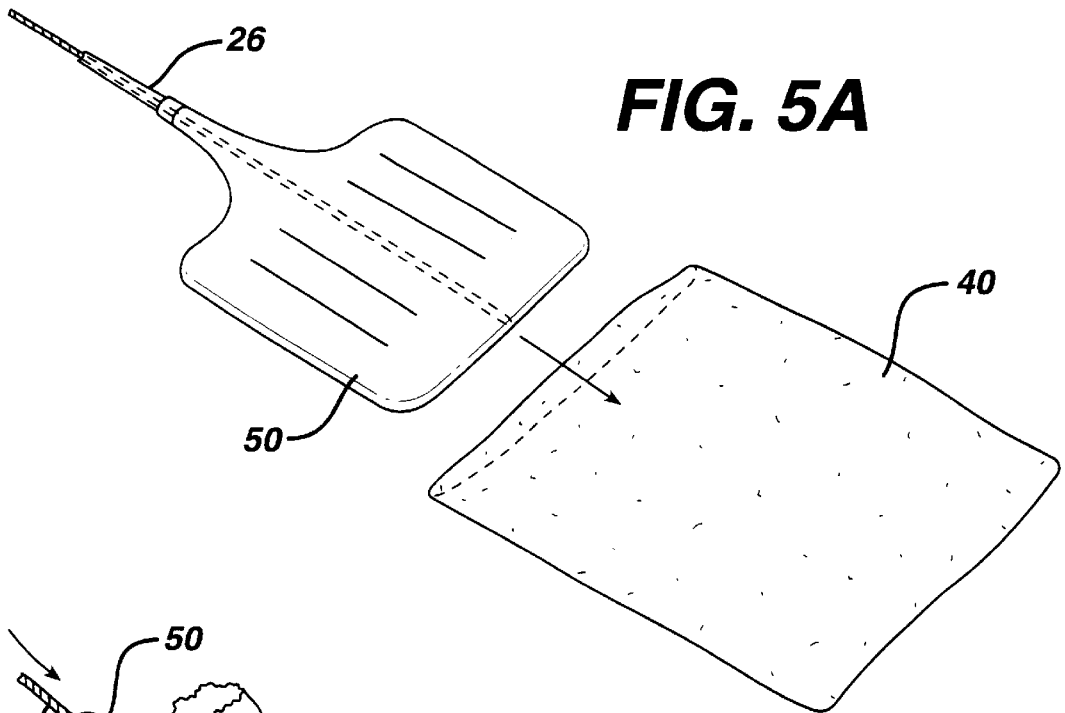
FIGS. 5A, 5B, and 5C schematically illustrate an alternative balloon system in which a collapsible balloon is removably disposed within an envelope of anti-adhesion material, and in which the balloon collapses to facilitate its removal from the positioned envelope.
Figure 5B:
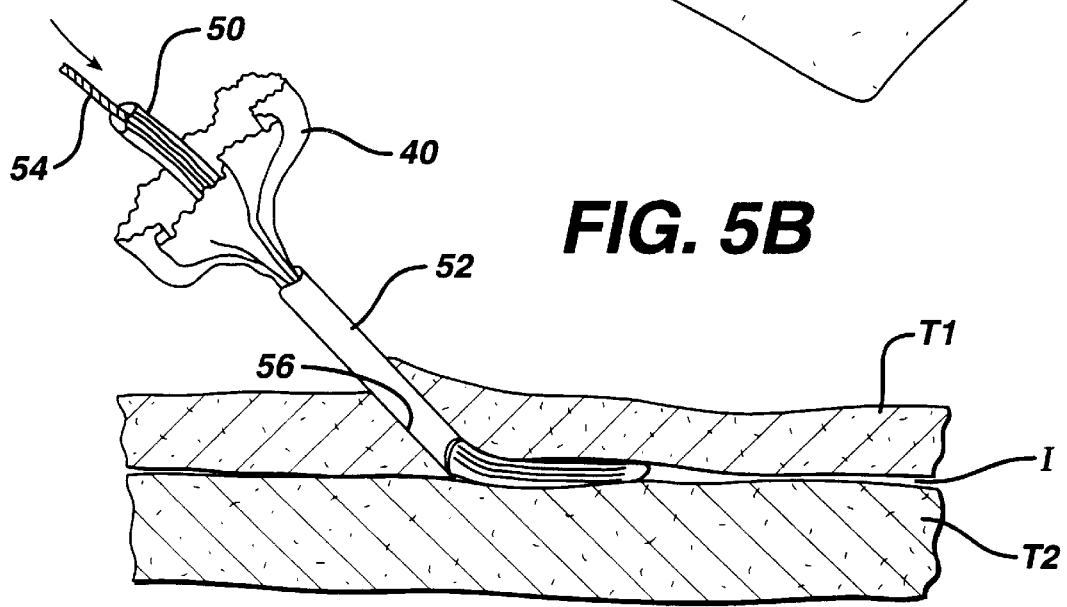
Figure 5C:
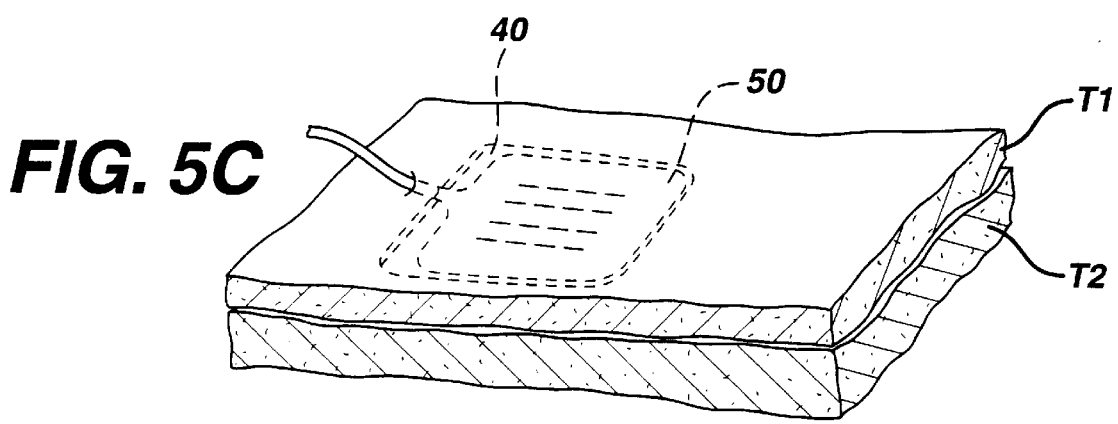

The method and system of the present invention can make use of a wide variety of alternative balloon structures, delivery methods, and surgical procedures. As an example, a balloon 50 having a structure similar to that described in U.S. Pat. No. 5,387,224, the full disclosure of which has previously been incorporated by reference, is removably insertable within an envelope 40. Balloon 50 compresses to a small-diameter configuration for insertion and/or removal through a cannula 52, the balloon optionally curling or compressing in accordion-like fashion. A flexible compression member 54 may facilitate advancing the balloon and envelope within tissue interface I. Alternatively, the balloon may simply be withdrawn proximally by tensioning tubular member 26 after the re-epithelialization period, and access wound 56 can generally be closed with a few sutures at the skin. Advantageously, balloon 50 positions and holds the anti-adhesion material of envelope 40 in position while inflated, combining mechanical separation and bio-active anti-adhesion efficacy with a minimally invasive post-operative balloon removal procedure, as can be understood with reference to FIGS. 5B and 5C.

Figure 6A:
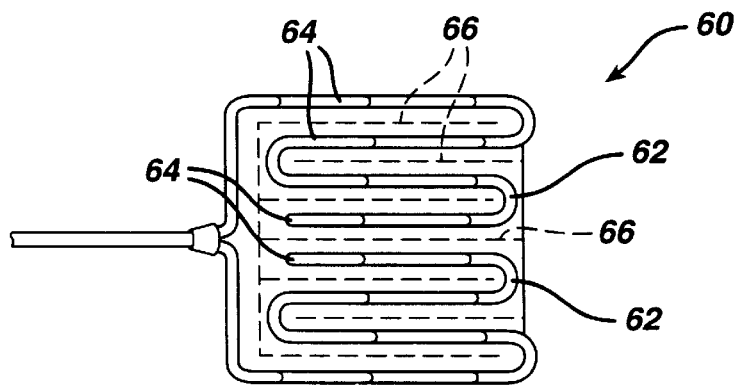
FIGS. 6A and 6B illustrate an alternative balloon system, in which a serpentine balloon forms a flat panel when inflated, and in which the adjacent balloon segments are coupled by frangible joints to facilitate removal.
Figure 6B:
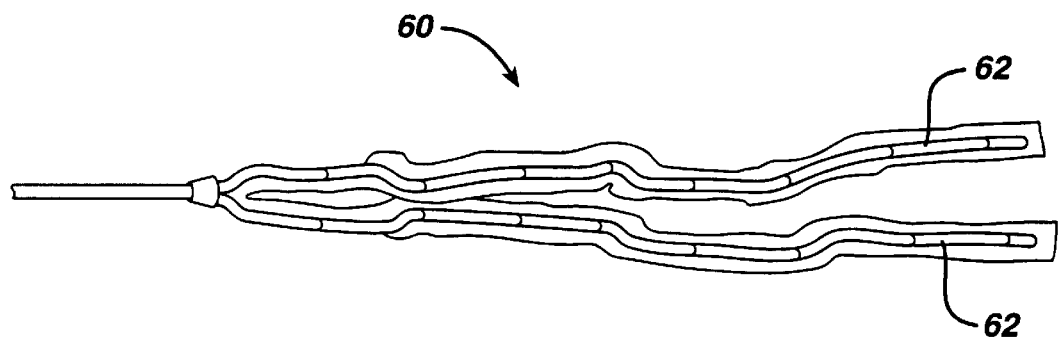

An alternative anti-adhesion balloon system is shown in FIGS. 6A and 6B. Serpentine balloon 60 is formed as one or more thin serpentine tubes 62, so that the balloon forms a substantially flat panel when inflated. Adjacent balloon segments 64 are coupled together by frangible joints 66. These joints may be score lines in a permanent or absorbable bio-active anti-adhesion film, or they may comprise weak connector materials or glues, or the like. Frangible joints 66 are broken as the balloon is withdrawn proximally, allowing the entire structure to be removed through a small opening. Serpentine balloon 60 is shown deflated in FIG. 6B after frangible joints 66 have been torn. The balloon need not form a contiguous panel when inflated, as intermittent mechanical separation of tissues between balloon segments may effectively disrupt adhesion formation. Hence, in some embodiments, adjacent balloon segments may be held in their relative positions in the panel by the shape of the balloon tube when inflated, rather than by frangible joints. Alternatively, serpentine balloon 60 may be disposed within an envelope of bio-active anti-adhesion film, as described above.

While the exemplary embodiment of the present invention has been described in some detail, for purposes of clarity and understanding, a wide variety of modifications and alternatives will be obvious to those who skill in the art. Therefore, the scope of the present invention is limited solely by the appended claims.

What is claimed is:

1. A method for interfering with formation of adhesions between two tissues, the tissues having nominal positions adjacent to each other within a patient body, the method comprising:

inflating a balloon to separate the tissues;

deflating the balloon to allow the tissues to return toward their nominal positions; and intermittently repeating the inflating and deflating steps during an adhesion prophylactic period.

2. A method as claimed in claim 1, wherein the deflating steps are repeated soon after the preceding inflating steps so that the balloon is deflated for more time than it is inflated.

3. A method as claimed in claim 1, wherein the inflating steps repeatedly disrupt fibrin which bridges the tissues.

4. A method as claimed in claim 3, wherein a time interval between sequential inflating steps is less than a time for formation of adhesion tissues bridging the tissues along the fibrin.

5. A method as claimed in claim 3, wherein the deflating step allows at least a portion of the separated tissues to substantially return to their nominal positions.

6. A method as claimed in claim 5, wherein a tissue separation region extends substantially beyond the balloon when the balloon is inflated.

7. A method as claimed in claim 1, further comprising positioning the balloon between the tissues adjacent an internal surgical site, closing the surgical site over the positioned balloon, and removing the balloon from the surgical site after the adhesion prophylactic period.

8. A method as claimed in claim 1 wherein the inflating step comprises actuating a subcutaneous pump which has been introduced through skin of the patient body.

9. A method as claimed in claim 1, further comprising covering at least a portion of the balloon with a bio-active anti-adhesion material.

10. A method for controlling tissue scar formation, the method comprising:
   inserting a balloon system into a patient body, wherein a bio-active anti-adhesion material is disposed between at least a portion of the balloon system and surrounding tissues;
   inflating the balloon within the patient body;
   deflating the balloon; and
   removing the balloon from the patient body.

11. A method as claimed in claim 10, wherein the anti-adhesion material is bio-absorbable, and wherein at least a portion of the anti-adhesion material remains within the body after the balloon is removed.

12. A method as claimed in claim 11, further comprising covering the balloon with an envelope formed of the anti-adhesion material, wherein the removing step comprises extracting the balloon from the envelope so that the anti-adhesion material remains in the body.

13. A method as claimed in claim 10, further comprising intermittently repeating the inflating and deflating steps during an adhesion prophylactic period.

14. A method as claimed in claim 10, wherein the balloon is continuously inflated to maintain mechanical separation of the tissues for an adhesion prophylactic period.

15. A system for controlling the formation of adhesions between nominally adjacent tissues, the system comprising:
   an implantable elastomeric balloon;
   a pressurization system in fluid communication with the balloon for repeatedly inflating and deflating the balloon so that the balloon intermittently separates the normally adjacent tissues.

16. A system as claimed in claim 15, wherein the pressurization system comprises a pump which is adapted to be implanted subcutaneously.

17. A system as claimed in claim 16, wherein the pump is actuatable through the skin when implanted.

18. A system as claimed in claim 15, wherein the balloon comprises an elastic material to dislodge fibrin forming on an outer surface of the balloon.

19. A system as claimed in claim 15, wherein the balloon comprises a substantially non-distensible inner body and a distensible toroid disposed circumferentially around the inner body, and wherein the toroid is inflatable from a small thickness to a large thickness to bluntly dissect adjacent tissues radially beyond the inner body.

20. A system as claimed in claim 15, further comprising an anti-adhesion material covering at least a portion of the balloon.

21. A system for controlling the formation of adhesions between nominally adjacent tissues within a patient body, the system comprising:
   a balloon which is implantable within the patient body, the balloon being inflatable to separate the nominally adjacent tissues;
   a pressurization system in fluid communication with the balloon for inflating the balloon; and
   a bio-active anti-adhesion material covering at least a portion of the balloon.

22. A system as claimed in claim 21, where the anti-adhesion material comprises a bio-absorbable envelope which removably covers the balloon.

23. A system for controlling the formation of adhesions between nominally adjacent tissues, the system comprising:
   an implantable balloon; and
   a pressurization system in fluid communication with the balloon for repeatedly inflating and deflating the balloon so that the balloon intermittently separates the normally adjacent tissues, wherein the pressurization system comprises a pump which is adapted to be implanted subcutaneously.

24. A system as claimed in claim 23, wherein the pump is actuatable through the skin when implanted.

25. A system for controlling the formation of adhesions between nominally adjacent tissues, the system comprising:
   an implantable balloon;
   wherein the balloon comprises a substantially non-distensible inner body and a distensible toroid disposed circumferentially around the inner body, and wherein the toroid is inflatable from a small thickness to a large thickness to bluntly dissect adjacent tissues radially beyond the inner body; and
   a pressurization system in fluid communication with the balloon for repeatedly inflating and deflating the balloon so that the balloon intermittently separates the normally adjacent tissues.

* * * * *